(12) United States Patent
Foster et al.

(10) Patent No.: US 9,610,041 B2
(45) Date of Patent: Apr. 4, 2017

(54) FIXATION MECHANISM ASSEMBLY AND METHOD FOR IMPLANTABLE DEVICES

(71) Applicant: Cardiac Pacemakers, Inc., St. Paul, MN (US)

(72) Inventors: Arthur J. Foster, Blaine, MN (US); Dana Sachs, Pine City, MN (US); Benjamin J. Haasl, Forest Lake, MN (US); Brian L. Schmidt, White Bear Lake, MN (US); Keith R. Maile, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 378 days.

(21) Appl. No.: 14/445,802

(22) Filed: Jul. 29, 2014

(65) Prior Publication Data

US 2015/0057520 A1 Feb. 26, 2015

Related U.S. Application Data

(60) Provisional application No. 61/867,673, filed on Aug. 20, 2013.

(51) Int. Cl.
*A61B 19/00* (2006.01)
*A61B 5/00* (2006.01)
(Continued)

(52) U.S. Cl.
CPC ........ *A61B 5/6882* (2013.01); *A61B 17/3403* (2013.01); *A61M 39/0208* (2013.01); *A61N 1/05* (2013.01); *A61N 1/0573* (2013.01)

(58) Field of Classification Search
CPC ............................ A61B 5/6879; A61B 5/6882
(Continued)

(56) References Cited

U.S. PATENT DOCUMENTS 5,540,648 A * 7/1996 Yoon .................. A61B 17/3403
600/102
7,212,870 B1 5/2007 Helland
(Continued)

FOREIGN PATENT DOCUMENTS

| IE | 2149449 A1 | 4/1972 |
| WO | 2005037055 A2 | 4/2005 |
| WO | 2012051235 A1 | 4/2012 |

OTHER PUBLICATIONS

Notification of Transmittal of the International Search Report and the Written Opinion of the International Searching Authority, or the Declaration for Application No. PCT/US2014/048628, 19 pages, date mailed Oct. 29, 2014.

*Primary Examiner* — John Lacyk
(74) *Attorney, Agent, or Firm* — Seager, Tufte & Wickhem, LLP.

(57) ABSTRACT

Fixation mechanism assemblies and methods are disclosed. A fixation mechanism assembly can include a first fixation member and a second fixation member moveably engaged with the first fixation member. The first fixation member can include a housing having a tissue facing surface and an opposing non-tissue facing surface, one or more guide apertures extending between the tissue facing surface and the non-tissue facing surface, and one or more first fixation elements. The first fixation member includes a longitudinal body and a proximal end attached to, or integrated with, the tissue facing surface of the housing. The second fixation member can include one or more second fixation elements. The second fixation element can correspond to a guide aperture and includes a longitudinal body, a proximal end attached to, or integrated with, the second fixation member, and a distal end movable through the corresponding guide aperture.

20 Claims, 12 Drawing Sheets

(51) Int. Cl.
*A61B 17/34* (2006.01)
*A61M 39/02* (2006.01)
*A61N 1/05* (2006.01)

(58) Field of Classification Search
USPC ............ 128/897–898; 600/372–373; 607/36, 607/116, 127; 604/174–175
See application file for complete search history.

(56) References Cited

U.S. PATENT DOCUMENTS

| | | |
|---|---|---|
| 7,553,298 B2 | 6/2009 | Hunt et al. |
| 7,762,998 B2 | 7/2010 | Birk et al. |
| 7,850,660 B2 | 12/2010 | Uth et al. |
| 7,901,381 B2 | 3/2011 | Birk et al. |
| 7,909,804 B2 | 3/2011 | Stats |
| 7,918,844 B2 | 4/2011 | Byrum et al. |
| 8,882,728 B2* | 11/2014 | Harders ................ A61F 5/003 600/37 |
| 2005/0038491 A1 | 2/2005 | Haack |
| 2005/0277899 A1* | 12/2005 | Conlon ................ A61F 5/0056 604/288.01 |
| 2012/0116489 A1 | 5/2012 | Khairkhahan et al. |
| 2012/0158111 A1 | 6/2012 | Khairkhahan et al. |
| 2012/0330392 A1 | 12/2012 | Regnier et al. |

\* cited by examiner

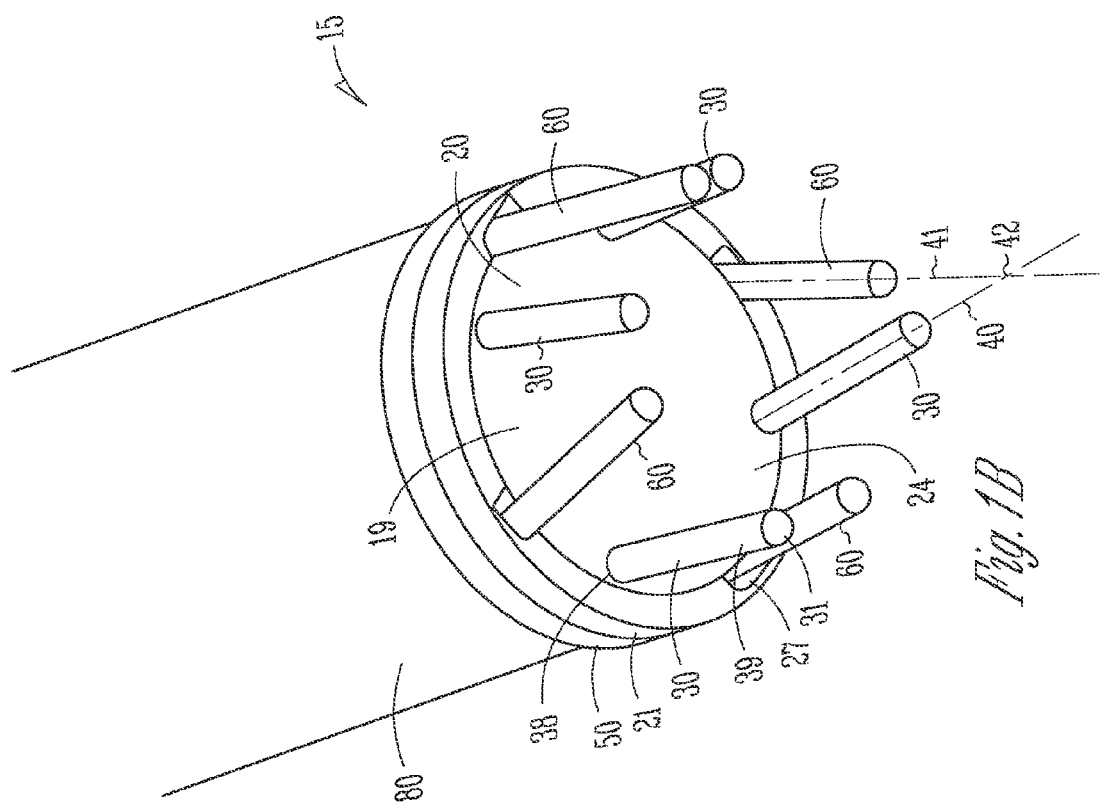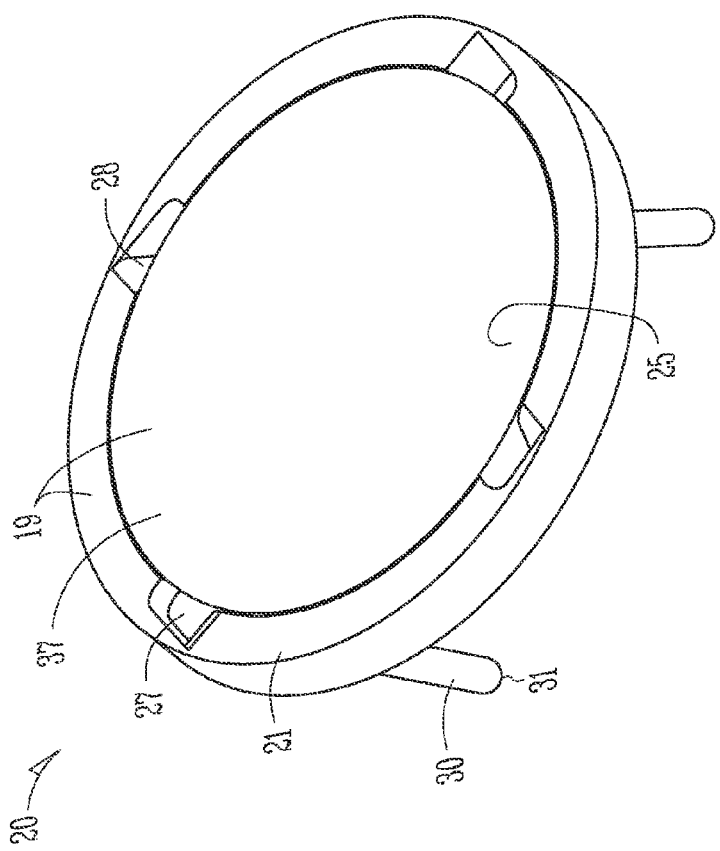

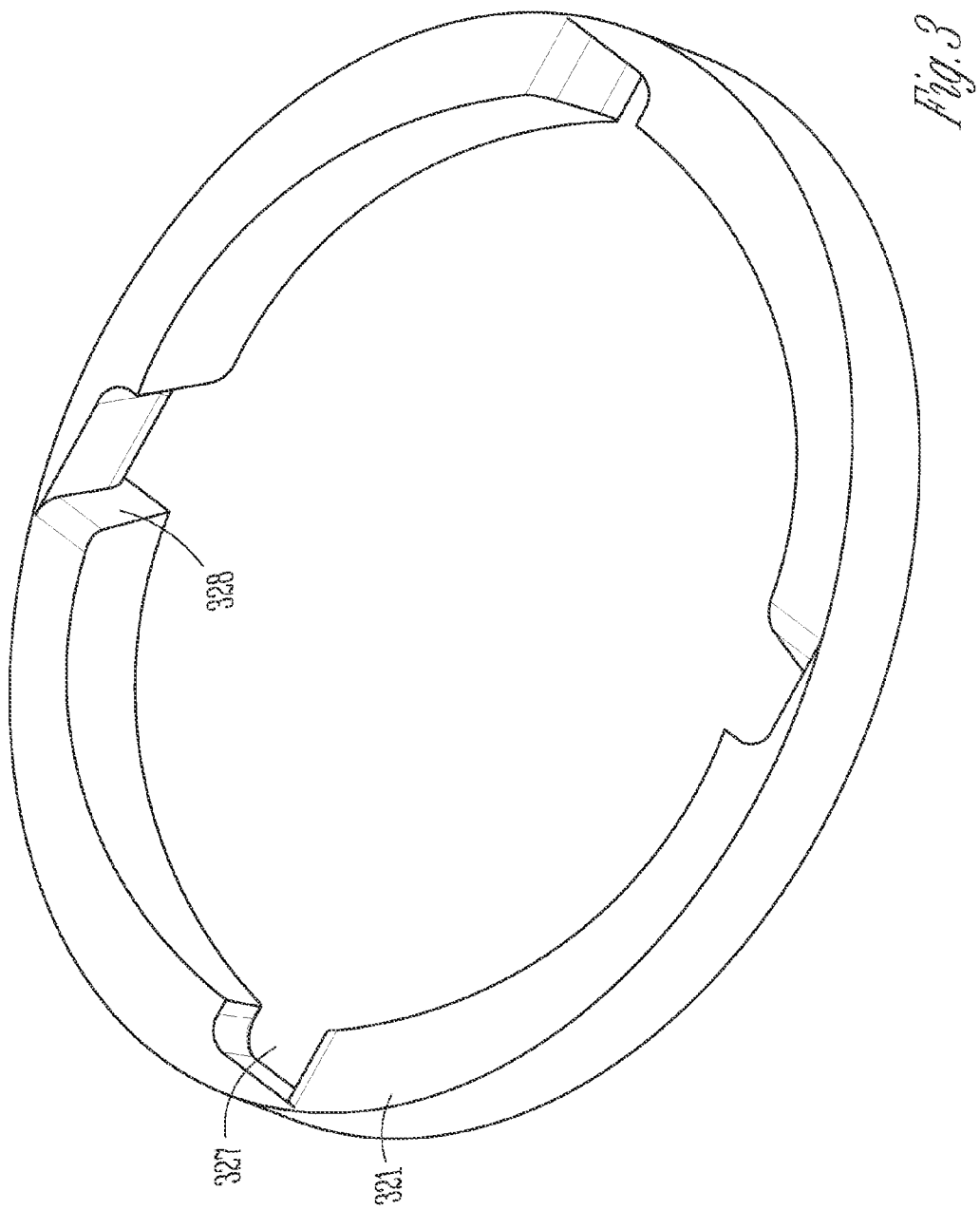

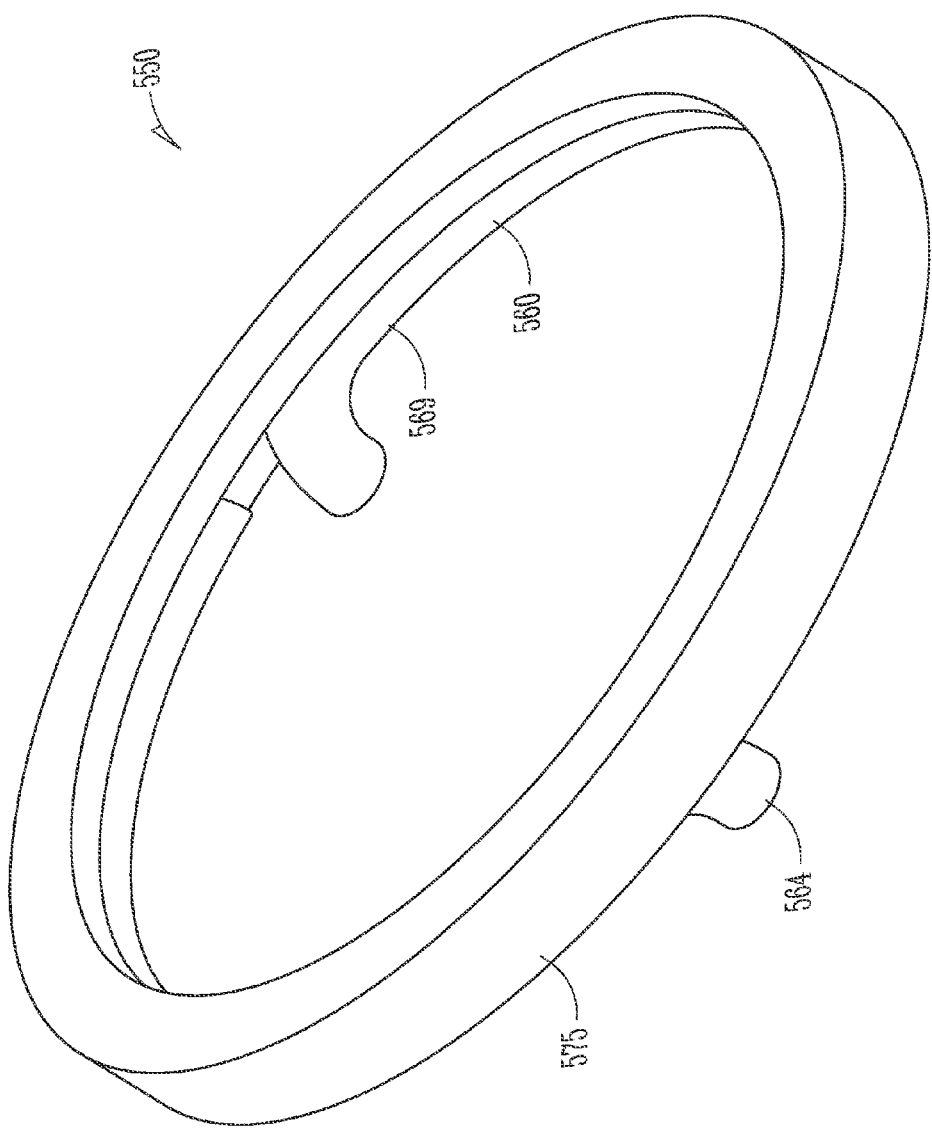

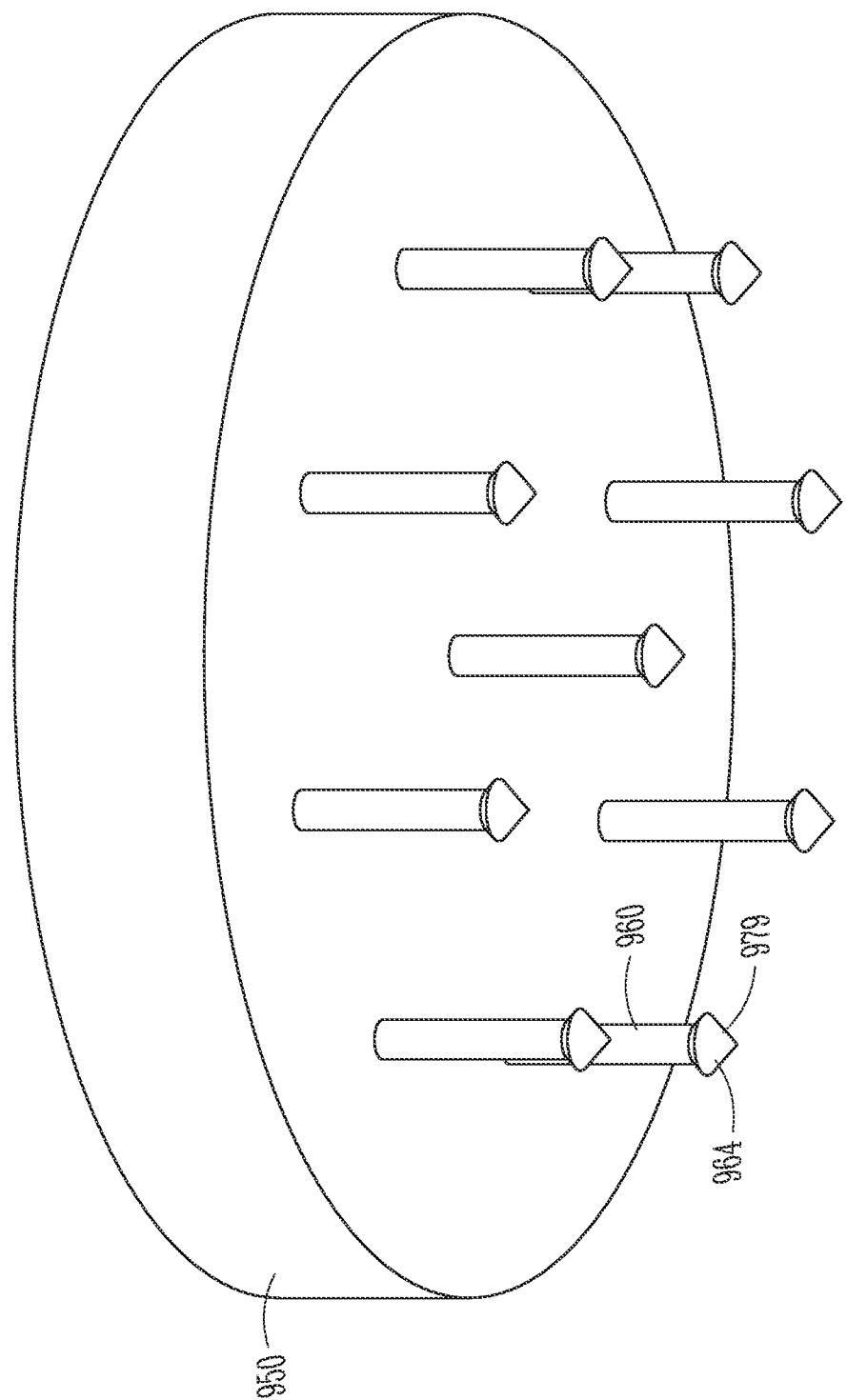

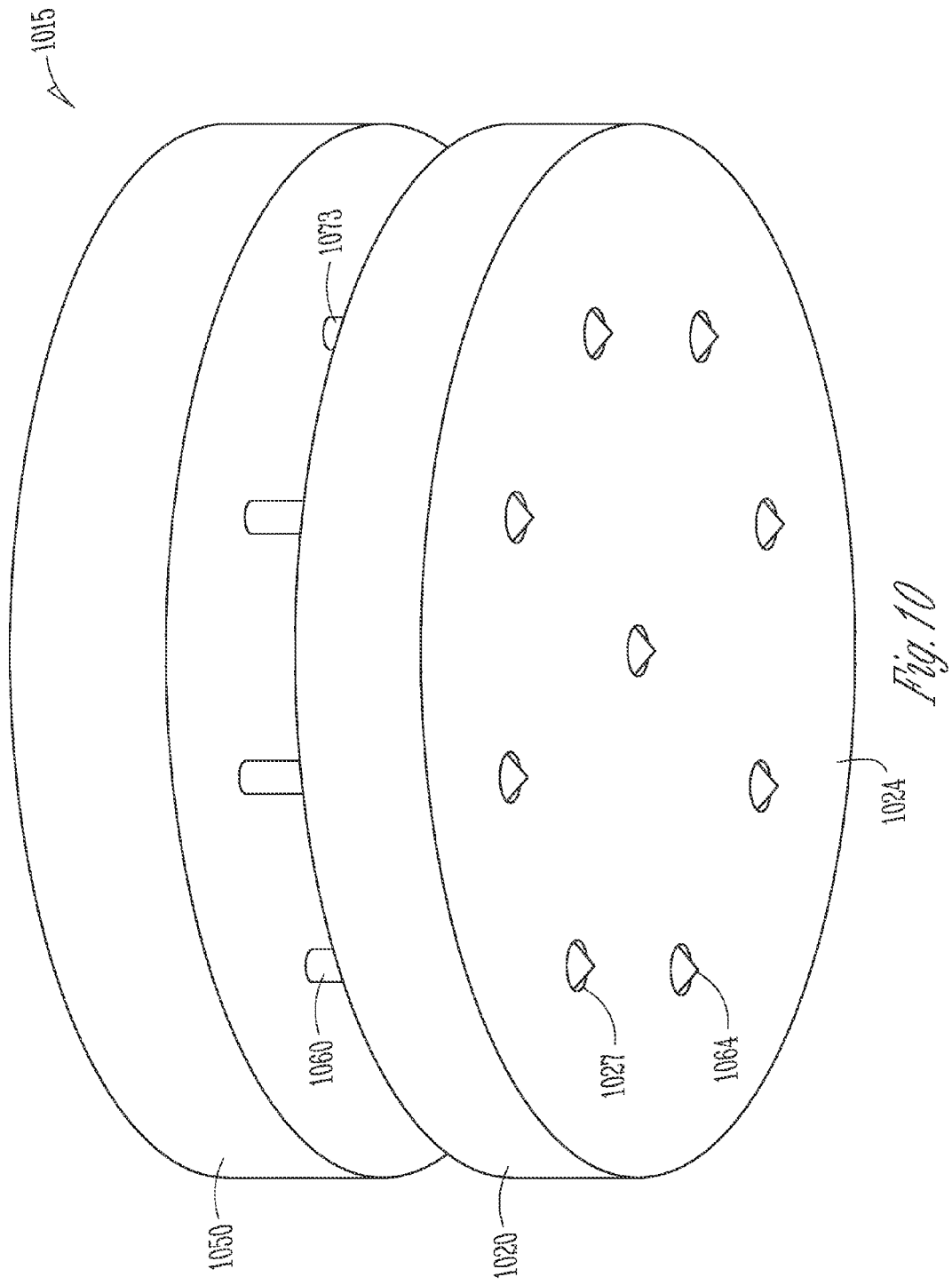

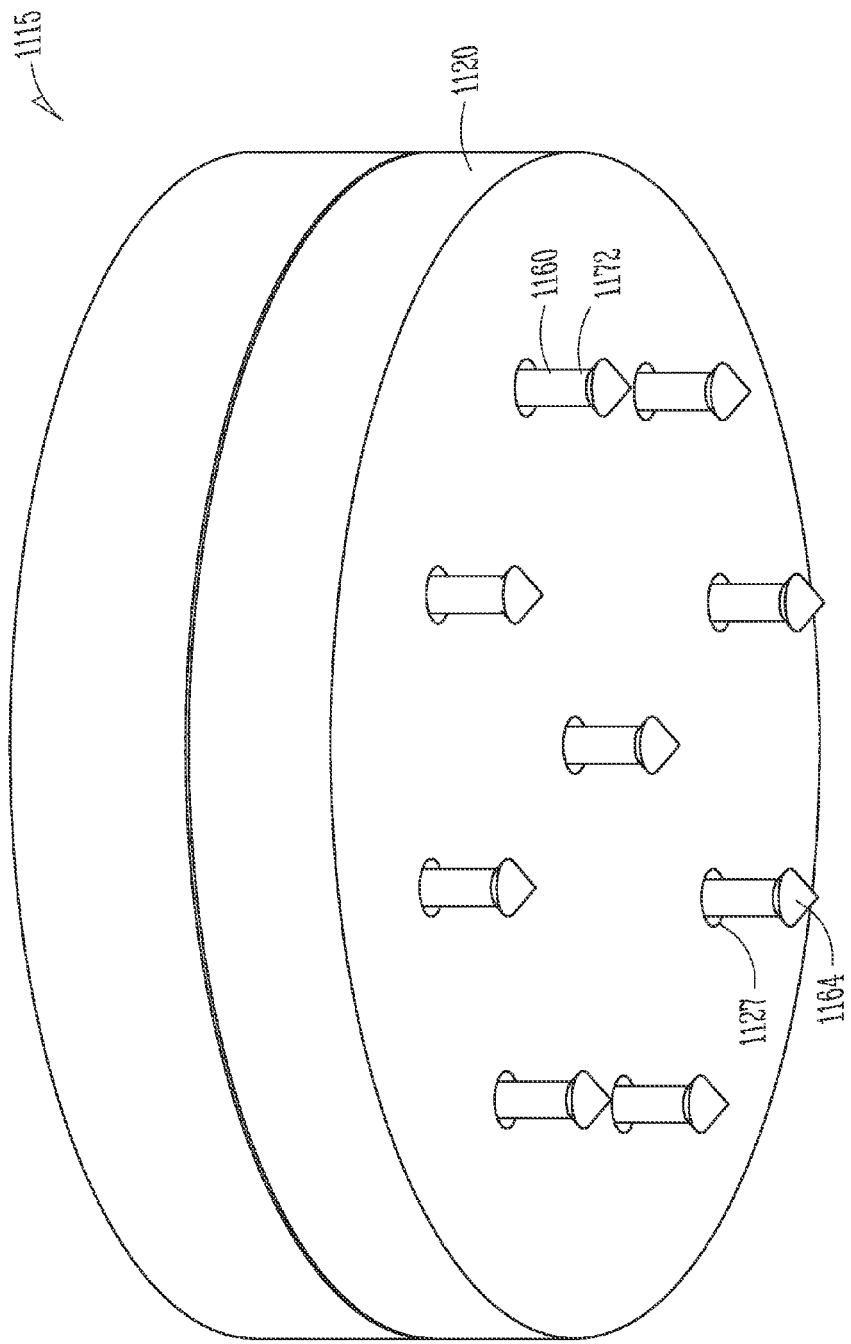

FIXATION MECHANISM ASSEMBLY AND METHOD FOR IMPLANTABLE DEVICES

CLAIM OF PRIORITY

This application claims the benefit of priority under 35 U.S.C. §119(e) of U.S. Provisional Patent Application Ser. No. 61/867,673, filed on Aug. 20, 2013, which is herein incorporated by reference in its entirety.

TECHNICAL FIELD

This document relates generally to medical devices, and more particularly, to assemblies and methods for fixing implantable devices to biological tissue.

BACKGROUND

Stimulation leads, sensing leads, and active devices including power supplies or electrodes need to be predictably and securely attached to targeted biological tissue to provide proper therapy. Some existing assemblies and methods to provide attachment for these devices are large, over-penetrate tissue, or generally irritate the tissue to which they are attached, resulting in adversely affected sensing or stimulation. Therefore, there is a need for new and improved fixation assemblies for implantable medical devices.

OVERVIEW

Implantable medical devices can be attached to biological tissue for stimulating or healing through electronic pulses or drug delivery, sensing tissue parameters (e.g., temperature, electronic state, movement, or chemical environment), or for structural containment purposes The present fixation mechanism assemblies and corresponding methods can include or use a first fixation member and a second fixation member moveably engaged with the first fixation member. The first fixation member can include a housing having a tissue facing surface and an opposing non-tissue facing surface, one or more guide apertures extending between the tissue facing surface and the non-tissue facing surface, and one or more first fixation elements. The first fixation element can include a longitudinal body and a proximal end attached to, or integrated with, the tissue facing surface of the housing. The second fixation member can include one or more second fixation elements. The second fixation element can correspond to the one or more guide apertures and can include a longitudinal body, a proximal end attached to, or integrated with, the second fixation member, and a distal end movable through the corresponding guide aperture.

To better illustrate the fixation mechanism assemblies and methods disclosed herein, a non-limiting list of examples is provided here:

In Example 1, a fixation mechanism assembly can comprise a first fixation member including a housing having a tissue facing surface and an opposing non-tissue facing surface, one or more guide apertures extending between the tissue facing surface and the non-tissue facing surface, and one or more first fixation elements. The one or more first fixation elements can include a longitudinal body, defining an axis, and a proximal end attached to, or integrated with, the tissue facing surface of the housing of the first fixation member. The fixation mechanism assembly can further include a second fixation member, moveably engaged with the first fixation member, including one or more second fixation elements. The one or more second fixation elements can correspond to the one or more guide apertures and include a longitudinal body, defining an axis, a proximal end attached to, or integrated with, the second fixation member, and a distal end movable through the one or more guide apertures.

In Example 2, the fixation mechanism assembly of Example 1 can optionally be configured such that at least one axis defined by the longitudinal body of the one or more first fixation elements intersects with at least one axis defined by the longitudinal body of the one or more second fixation elements.

In Example 3, the fixation mechanism assembly of any one or any combination of Examples 1 or 2 can optionally be configured such that the longitudinal body of the one or more first fixation elements includes a fixed length and a fixed angle, relative to the tissue facing surface of the housing of the first fixation member.

In Example 4, the fixation mechanism assembly of any one or any combination of Examples 1-3 can optionally be configured such that at least one of the one or more first fixation elements includes a rigid polymer and is electrically neutral.

In Example 5, the fixation mechanism assembly of any one or any combination of Examples 1-4 can optionally be configured such that the one or more guide apertures are located around a perimeter of the first fixation member.

In Example 6, the fixation mechanism assembly of any one or any combination of Examples 1-5 can optionally be configured such that the one or more second fixation elements are positioned to collectively surround the one or more first fixation elements.

In Example 7, the fixation mechanism assembly of any one or any combination of Examples 1-6 can optionally be configured such that a housing of the second fixation member is positioned adjacent the non-tissue facing surface of the housing of the first fixation member.

In Example 8, the fixation mechanism assembly of any one or any combination of Examples 1-7 can optionally be configured such that each of the one or more second fixation elements are extendable from, and retractable within, the tissue facing surface of the housing of the first fixation member through relative rotation between the first and second fixation members.

In Example 9, the fixation mechanism assembly of any one or any combination of Examples 1-8 can optionally be configured such that one or both of the first and second fixation members includes a stop feature configured to limit relative movement between the members.

In Example 10, the fixation mechanism assembly of any one or any combination of Examples 1-9 can optionally be configured such that at least one of the one or more second fixation elements is electrically neutral.

In Example 11, the fixation mechanism assembly of any one or any combination of Examples 1-10 can optionally be configured such that at least one of the one or more second fixation elements includes a shape memory alloy.

In Example 12, the fixation mechanism assembly of any one or any combination of Examples 1-11 can optionally be configured such that each of the one or more second fixation elements are configured to be deployed into a tissue site through rotation of the second fixation member relative to the first fixation member, and wherein, after deployment of the one or more second fixation elements, the axis defined by at least one of the one or more second fixation elements crosses the axis defined by at least one of the one or more first fixation element.

In Example 13, the fixation mechanism assembly of any one or any combination of Examples 1-12 can optionally be configured such that at least one of the one or more first or second fixation elements includes a radiopaque material.

In Example 14, the fixation mechanism assembly of any one or any combination of Examples 1-13 can optionally be configured to further comprise a fixation device configured to hold stationary one of the first fixation member and the second fixation member and rotate the other one of the first fixation member and the second fixation member.

In Example 15, a method of tissue fixation can comprise engaging a first fixation member and a second fixation member; positioning the first and second fixation members over a tissue site; engaging one or more first fixation elements, attached to or integrated with the first fixation member, to the tissue site; and moving one of the first fixation member and the second fixation member relative to the other one of the first fixation member and the second fixation member to deploy one or more second fixation elements that are attached to or integrated with the second fixation member through one or more apertures defined in the first fixation member and into the tissue site.

In Example 16, the method of Example 15 can optionally be configured such that moving one of the first fixation member and the second fixation member relative to the other one of the first fixation member and the second fixation member includes rotating one of the first fixation member and the second fixation member relative to the other one of the first fixation member and the second fixation member.

In Example 17, the method of any one or any combination of Examples 15-16 can optionally be configured such that deploying the one or more second fixation elements includes establishing a plurality of points of fixation between the first and second fixation members and the tissue site.

In Example 18, the method of any one or any combination of Examples 15-17 can optionally be configured to further comprise using at least one of the one or more first fixation elements or the one or more second fixation elements to sense or stimulation the tissue site.

In Example 19, the method of any one or any combination of Examples 15-18 can optionally be configured to further comprise retracting the one or more second fixation elements from the tissue site through movement of the first fixation member or the second fixation member in a direction opposite the movement leading to deployment.

In Example 20, a fixation mechanism assembly can comprise a first fixation member including a housing having a tissue facing surface and an opposing non-tissue facing surface, one or more guide apertures extending between the tissue facing surface and the non-tissue facing surface, and a fixation means to attach the first fixation member to a body surface. The fixation mechanism assembly can further include a second fixation member, moveably engaged with the first fixation member, including one or more fixation elements. The one or more fixation elements corresponding to the one or more guide apertures can include a longitudinal body, defining an axis, a proximal end attached to, or integrated with, the second fixation member, and a distal end movable through the one or more guide apertures.

In Example 21, the fixation mechanism assembly or method of tissue fixation of any one or any combination of Examples 1-20 can optionally be configured such that all elements, operations, or other options are available to use or select from.

These and other examples and features of the present fixation mechanism assemblies and corresponding methods will be set forth in part in the following Detailed Description. This Overview is intended to provide non-limiting examples of the present subject matter—it is not intended to provide an exclusive or exhaustive explanation. The Detailed Description below is included to provide further information about the present fixation mechanism assemblies and corresponding methods.

BRIEF DESCRIPTION OF THE DRAWINGS

In the drawings, like numerals can be used to describe similar elements throughout the several views. Like numerals can be used to represent different views or configurations of similar elements. The drawings illustrate generally, by way of example, but not by way of limitation, various embodiments discussed in the present document.

FIG. 1A illustrates an example of a first fixation member, as constructed in accordance with at least one embodiment.

FIG. 1B illustrates an example of a fixation mechanism assembly, including the first fixation member of FIG. 1A, a second fixation member, and a fixation device, as constructed in accordance with at least one embodiment.

FIG. 3 illustrates an example of a ring member of the first fixation member of FIG. 1A, as constructed in accordance with at least one embodiment.

FIG. 5 illustrates an example of a second fixation member, as constructed in accordance with at least one embodiment.

FIGS. 9-11 illustrate a fixation mechanism assembly configured for non-rotational deployment of one or more second fixation elements, as constructed in accordance with at least one embodiment.

DETAILED DESCRIPTION

Figure 2:
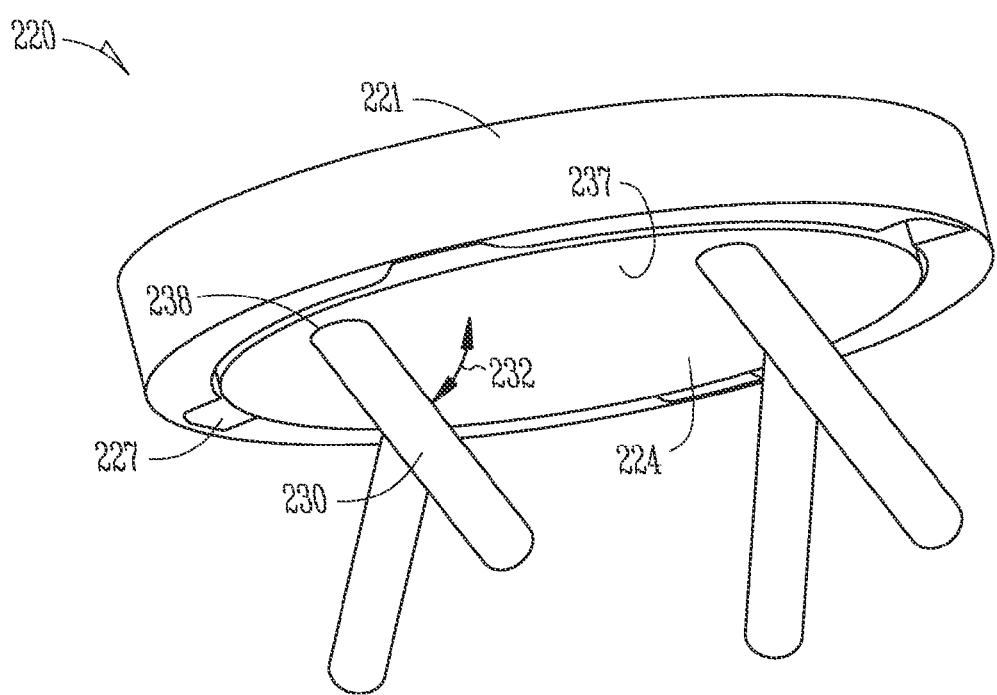
FIG. 2 illustrates an example of a first fixation member viewed from a tissue engaging surface, as constructed in accordance with at least one embodiment.

A target site for the present fixation mechanism assemblies and corresponding methods can include tissue or a body organ, such as an interior or exterior of an artery or vein, a nerve bundle, skin, a carotid body, a stomach or intestine, a bladder, a kidney, soft tissue, gastric tissue, or neural tissue. The target site can also include an epicardial or endocardial site.

FIG. 1A illustrates an example of a first fixation member 20. FIG. 1B illustrates an example of a fixation mechanism assembly 15 including the first fixation member 20 of FIG. 1A, a second fixation member 50, and a fixation device 80.

The first fixation member 20 can include one or more first fixation elements 30. The first fixation element 30 can include a longitudinal body 39 extending from a first end 38, attached to or integrated with a housing 19 of the first fixation member 20, to an opposite tissue engaging end 31. The first fixation element 30 can have a fixed shape and a fixed angle of attachment or integration with the housing 19. Materials that can be used for the one or more first fixation elements 30 can include plastics, such as PEEK or polysulfone, and biometals, such as stainless steel, Elgiloy, MP35N, Platinum, Palladium, Titanium, Nitinol or composites or alloys of these metals, or other materials suitable for use as fixation elements. The one or more first fixation elements can be sized, shaped, or otherwise configured to allow the fixation mechanism assembly 15 to be chronically and securely affixed to targeted tissue, such as an epicardial or endocardial surface of a heart.

The housing 19 of the first fixation member 20 can be generally planar and can include a non-tissue facing surface 25 and an oppositely located tissue facing surface 24. To encourage close contact between the tissue facing surface 24 and the targeted tissue, the first fixation member 20 can be sized, shaped, or otherwise configured to lay flat against, or conform to, a surface of a heart or other organ. In an example, the tissue facing surface 24 of the first fixation member 20 can have a concave, convex, or other curved shape that can match, approximate, or conform to the contour of an of an implantation site. In an example, a width of the first fixation member 20 can be greater than a height of the first fixation member 20.

In an example, the tissue facing surface 24 can have a diameter of approximately 2-80 millimeters, and a surface area of approximately 6-250 square millimeters. In an example, the tissue facing surface 24 can have a diameter of approximately 3-60 millimeters, and a surface area of approximately 7-200 square millimeters. In an example, the tissue facing surface 24 can have a diameter of approximately 4-40 millimeters, and a surface area of approximately 12-120 square millimeters. In an example, the tissue facing surface 24 can have a diameter of approximately 5-30 millimeters, and a surface area of approximately 15-90 square millimeters. In an example, the tissue facing surface 24 can have a diameter of approximately 6-20 millimeters, and a surface area of approximately 18-60 square millimeters. In an example, the tissue facing surface 24 can have a diameter of approximately 7-15 millimeters, and a surface area of approximately 21-45 square millimeters. In an example, the tissue facing surface 24 can have a diameter of approximately 8-10 millimeters, and a surface area of approximately 24-30 square millimeters. In an example, the tissue facing surface 24 can have a diameter of approximately 2-10 millimeters, and a surface area of approximately 6-30 square millimeters. In an example, the tissue facing surface 24 can have a diameter of approximately 2-6 millimeters, and a surface area of approximately 6-20 square millimeters.

The housing 19 of the first fixation member 20 can be circular in shape and can include a ring member 21 and a base 37. The base 37 can be centrally located and provide a structural area for additional devices or attachment fixtures, an attachment area for one or more first fixation elements 30, or include engaging features for movement between the ring member 21 and the base 37. In an example, the ring member 21 can surround and be moveable relative to the base 37. In another example, the ring member 21 can be fixed relative to the base 37.

The first fixation member 20 can include one or more guide apertures 27. The guide apertures 27 can provide a pathway for one or more second fixation elements 60 attached to, or integrated with, a housing of the second fixation member 50. The second fixation elements 60 can be moveable and can be deployed from, or retracted within, the second fixation member 50. The guide apertures 27 can each include one or more aperture angles 28, which can serve to direct deployment of a second fixation element 60 in a desired direction. The aperture angle 28 can include angled surfaces configured to direct movement of the second fixation element 60. The one or more guide apertures 27 can be located around a perimeter of the first fixation member 20, such as in the ring member 21, however in other instances, can be provided in other portions of the first fixation member 20.

Relative movement between the one or more guide apertures 27 and the second fixation member 50 can cause the one or more second fixation elements 60 to deploy or retract. The first fixation element 30 can include a first longitudinal axis 40 extending centrally through the longitudinal body 39. Each second fixation element 60 can include a second longitudinal axis 41. The first fixation elements 30 and the second fixation elements 60 can be configured such that, when the second fixation elements 60 are deployed, at least one of the first longitudinal axis 40 and at least one of the adjacent second longitudinal axes 41 can cross at an axes intersection 42.

The fixation mechanism assembly 15 can further include the fixation device 80. The fixation device 80 can be configured to hold stationary one of the first fixation member 20 and the second fixation member 50, while concurrently moving the other one of the first fixation member 20 and the second fixation member 50. In an example, the fixation device 80 can be configured to hold the first fixation member 20 stationary, while concurrently translating, rotating, or otherwise moving at least portion of the second fixation member 50. In an example, the fixation device 80 can be configured to hold the second fixation member 50 stationary, while concurrently translating, rotating, or otherwise moving at least a portion of the first fixation member 20. In another example, the fixation device 80 can provide relative movement between the first fixation member 20 and the second fixation member 50

FIG. 2 illustrates a first fixation member 220 viewed from a tissue facing surface 224. The first fixation member 220 can include at least one first fixation element 230 having a first end 238 attached to, or integrated with, a housing of the first fixation member 220. The at least one first fixation element 230 can include a passive fixation element, an active fixation element, a combination of one or more passive or active fixation elements, or biocompatible adhesive, such as a glue. Examples of passive fixation elements can include one or more tines, one or more fins, or one or more other extension structures. Examples of active fixation elements can include one or more screws, one or more hooks, one or more barbs, one or more helices, or one or more other tissue-penetrating mechanisms. In an example, the at least one first fixation element 230 can include a small wire or pin with a fixed angle 232. The preceding are all means of attaching the first fixation member to a body surface.

In an example, the first fixation member 220 can include a housing having a base 237 and a surrounding ring member 221. The base 237 can have attachment regions for the at least one first fixation element 230. The ring member 221 can be located outside of the base 237 and can be configured to move relative to the base 237. In another example, the ring member 221 can be fixed relative to the base 237. One or more guide apertures 227 can be positioned in the first fixation member 220 and can include an aperture passing from a non-tissue facing surface 25 (FIG. 1A) to the tissue facing surface 224. In an example, the guide apertures 227 can be located in the ring member 221.

FIG. 3 illustrates an example of a ring member 321 of a first fixation member. The ring member 321 can include one or more guide apertures 327 having an aperture angle 328 arranged to direct movement of one or more second fixation elements 60 (FIG. 1B). In an example, the aperture angle 328, measured from the generally horizontal plane of the ring member 321 to the direction of the guide aperture 327 ranges from 5-90 degrees. In an example, the aperture angle 328 ranges from 5-80 degrees. In an example, the aperture angle 328 ranges from 10-70 degrees. In an example the aperture angle 328 ranges from 20-60 degrees. In an example, the aperture angle 328 ranges from 30-50 degrees. In an example, the aperture angle 328 is about 15 degrees. In an example, the aperture angle 328 is about 30 degrees. In an example the aperture angle 328 is about 45 degrees. In an example, the aperture angle 328 is about 60 degrees. The preceding angle ranges can be used for locations of the aperture at other locations in addition to the ring member 321, such as in the fixation mechanisms described in FIGS. 6-11. The ring member 321 can include any number of guide apertures 327, such as 2, 3, 4, 5, 6, 7, or 8 guide apertures 327.

Figure 4A:
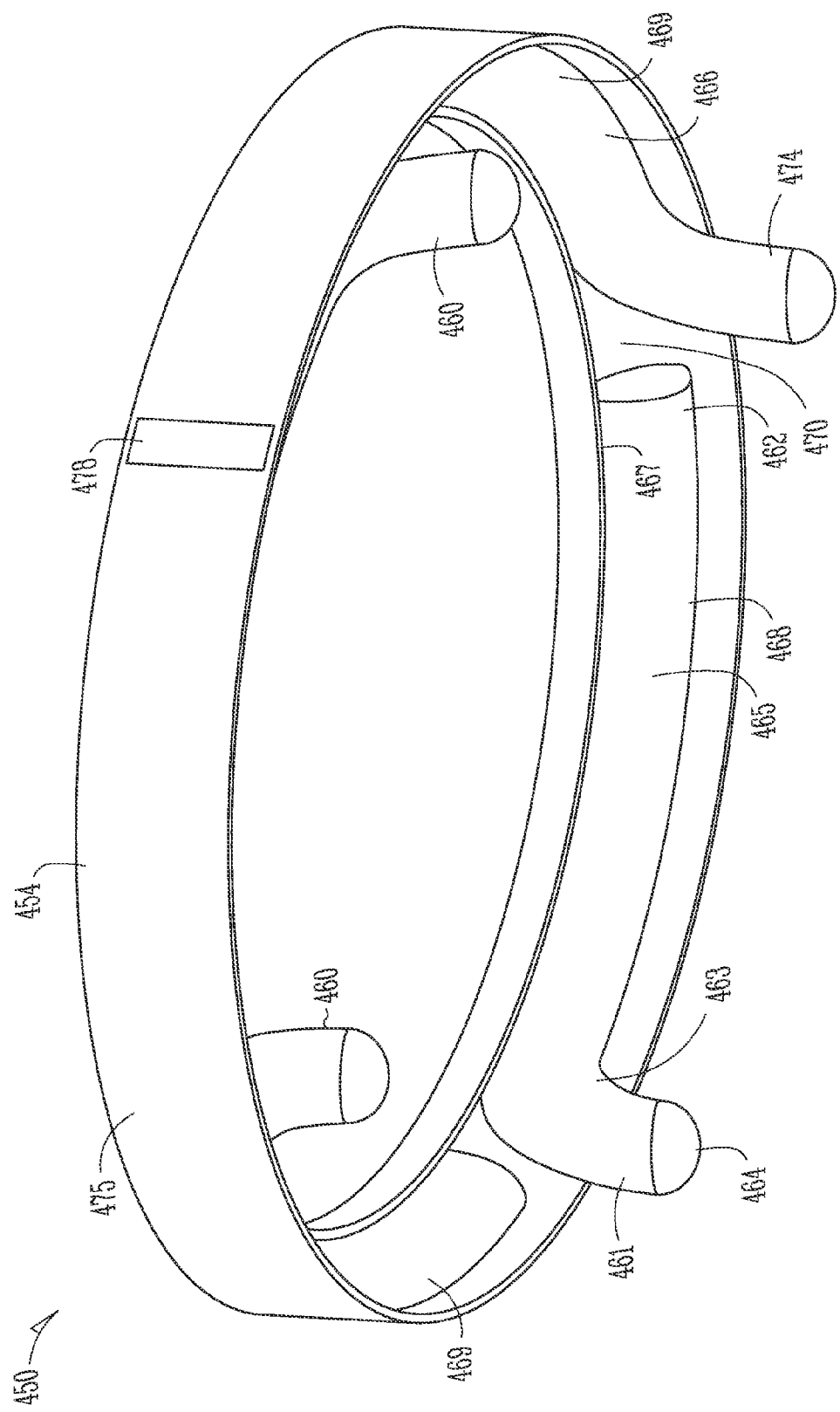
FIG. 4A illustrates an example of a second fixation member, as constructed in accordance with at least one embodiment.

FIG. 4A illustrates an example of a second fixation member 450 including one or more second fixation elements 460 and a second housing 454. The second housing 454 can serve as a structural framework for attaching the one or more second fixation elements 460. In an example, the second housing 454 can contain sensing or stimulation devices. In an example, the second housing 454 can be ring shaped, but, in other examples, it can be disk shaped, rectangular, or any polygonal shape. Materials that can be used for the one or more second fixation elements 460 and for the second housing 454 can include plastics, such as PEEK or polysulfone, and biometals, such as stainless steel, Elgiloy, MP35N, Platinum, Palladium, Titanium, Nitinol or composites or alloys of these metals.

At least a portion of the one or more second fixation elements 460 can be made of a shape memory alloy 466. The shape memory alloy 466 can be configured to alter its shape depending on parameters including temperature or stress loading. For example, the one or more second fixation elements 460 can be configured to have an initial shape to conform to a loaded position 469, engaged with a receiving shape 470 of an outer housing body 475, and can include a second bend area 465. The loaded position 469 can be similar to a retracted position, but can include stress loading that can define the shape of a retracted second fixation element 460. The one or more second fixation elements 460 can be configured, using shape memory alloys, to have a subsequent shape (e.g., straightened shape) once deployed from the confines of the second fixation member 450. Each second fixation element 460 can include a longitudinal body 468 extending from a second fixation element distal end 461 to a second fixation element proximal end 462. In a region near its proximal end 462, each second fixation element 460 can include a second fixation attachment 467 to the second housing 454. The attachment can be attained through welding, gluing, or fastening, or the second fixation element 460 can be manufactured integrally with the housing 454.

The second fixation element 460 can include a first bend area 463 to allow its tip 464 to be positioned in a guide aperture 27 (FIG. 1A). Since a major portion of each second fixation element 460 is unattached to the second housing 454, relative movement between the second fixation member 450 and a first fixation member 20 (FIG. 1A) can cause one or more second fixation elements 460 to be deployed outwardly. The outward deployment of the one or more second fixation elements 460 can cause the tips 464 to penetrate targeted tissue. As one or more guide apertures 27 (FIG. 1) are rotated, translated, or otherwise moved from a position near the tips 464 towards a position near the second fixation element attachment sites 467, the second fixation elements 460 can pass through the guide apertures. In an example, the relative movement can be accomplished by moving the second fixation member 450. In another example, the relative movement can be accomplished by moving at least a portion of the first fixation member 20, such as moving the ring member 21 (FIG. 1A). In another example, the ring member 21 can be fixed relative to a base 37 of the first fixation member 20 and the first fixation member 20 can be moved as a unit.

The second fixation member 450 can include a radiopaque marking 478 or include a radiopaque material. The radiopaque marking 478 can be included in a housing 454 to locate a position of the second fixation member 450 relative to a position of the first fixation member 20. One or more of the second fixation elements 460 can include a radiopaque marking or material 474 to locate a position or shape of the second fixation elements 460. The first fixation elements if FIGS. 1-3 and 6-11 can also include similar radiopaque markings or materials.

A length of the one or more second fixation elements 460 that is deployed during installation of a fixation mechanism assembly 15 (FIG. 1B) can be limited by one or more of: 1) the second fixation element attachment point 467, 2) one or more detents between the first fixation member 20 and the second fixation member 450, 3) rotational or movement stops located at a proximal end of a fixation device 80 (FIG. 1B), 4) rotational or movement stops located at or near the engagement of the first fixation member 20 and the second fixation member 450, 5) a restriction of movement between the first fixation member 20 and the second fixation member 450, when a distal surface of the second fixation member engages a non-tissue facing surface of the first fixation member (FIG. 10), or 6) manual limitation aided by radiologic or imaging techniques.

In the example of FIG. 4A, the four second fixation elements 460 do not overlap each other in the loaded position 469.

Figure 4B:
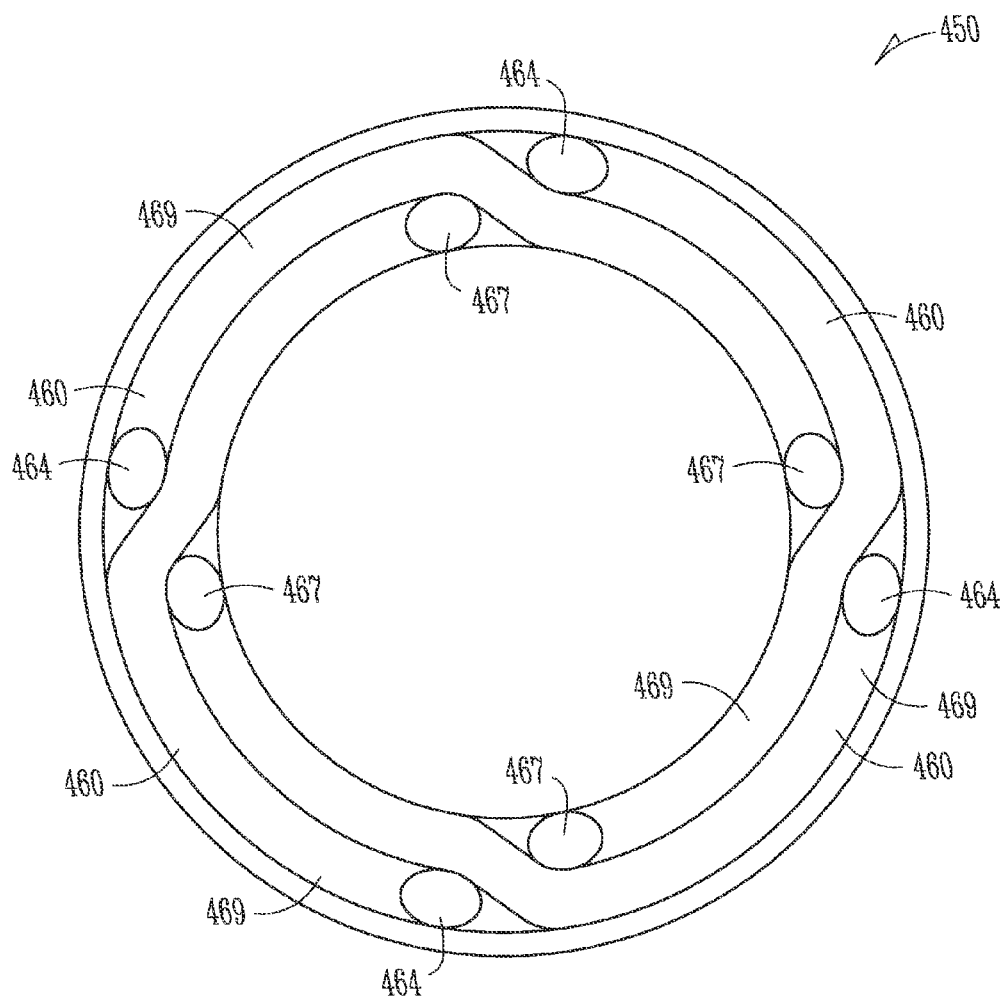
FIG. 4B illustrates a schematic view of one or more second fixation elements included in an example of a second fixation member, as constructed in accordance with at least one embodiment.

In the example of FIG. 4B, one or more second fixation elements 460 are arranged in an overlapping loaded position 469. The second fixation elements 460 can overlap each other such that a total length from a tip 464 to an attachment point 467 can be longer than a non-overlapping example of similar dimensions. As the second fixation member 450 is translated, rotated, or otherwise moved relative to a first fixation member 20 (FIG. 1A), the one or more second fixation elements 460 can be deployed with a majority of their length passing through one or more guide apertures 27 of the first fixation member 20. An overlapping loaded configuration, such as is illustrated in FIG. 4B, can give a deployed length of the one or more second fixation elements 460 that is greater than a corresponding non-overlapping loaded configuration.

FIG. 5 illustrates a second fixation member 550 including two second fixation elements 560, instead of four fixation elements as in FIGS. 4A and 4B. The second fixation elements 560 can conform to a shape of an outer housing body 575 of the second fixation member 560, when in a retracted and loaded position 569.

Figure 6:
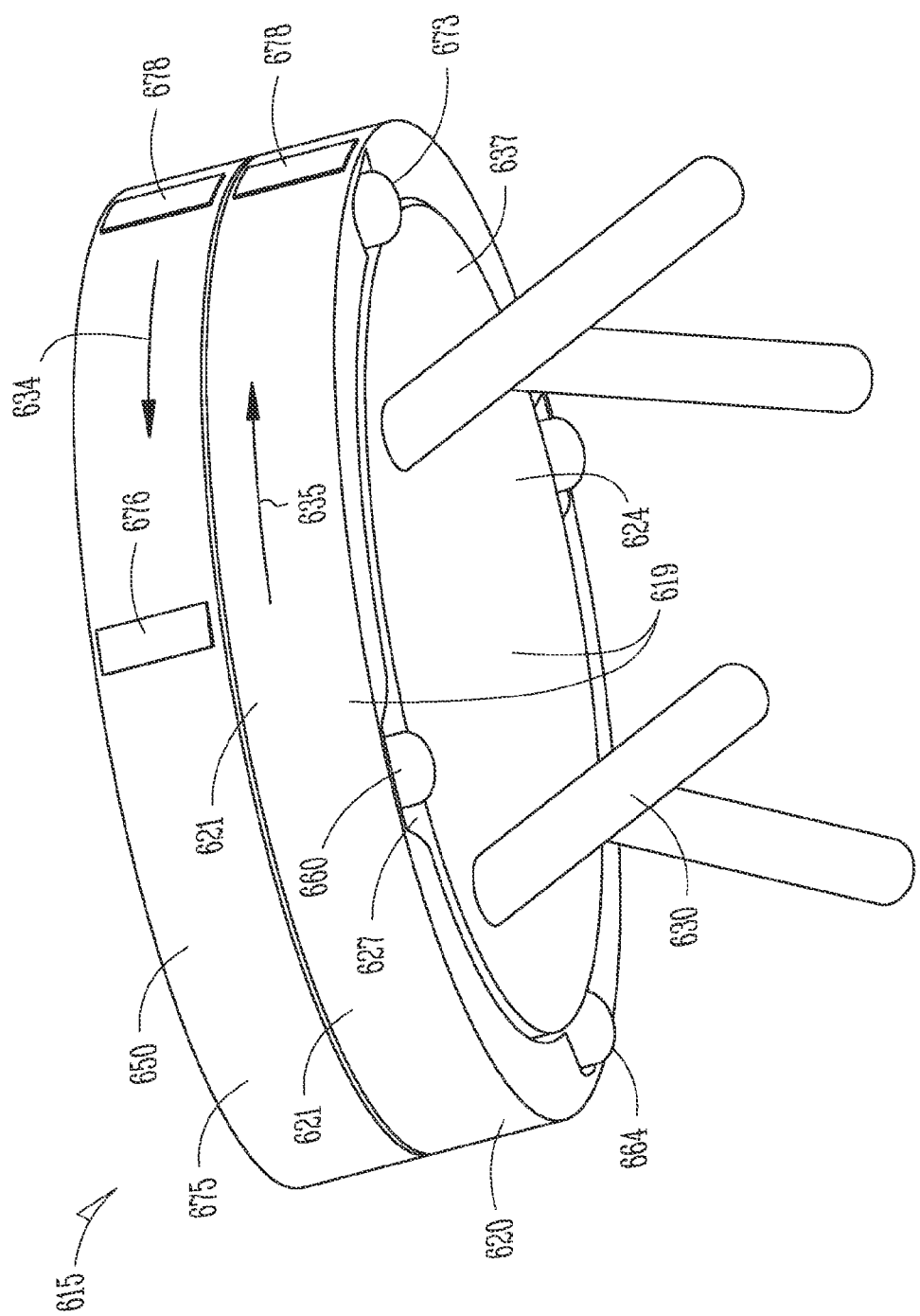
FIG. 6 illustrates an example of a fixation mechanism assembly with one or more second fixation elements in a retracted position, as constructed in accordance with at least one embodiment.

FIG. 6 illustrates a fixation mechanism assembly 615 including a first fixation member 620 and a second fixation member 650. The first fixation member 620 can include a first housing 619 having a base 637, to which one or more first fixation elements 630 can be attached or integrated, and a surrounding ring member 621. The first housing 619 can include a tissue facing surface 624 and an opposing non-tissue facing surface. The ring member 621 can include one or more guide apertures 627.

The second fixation member 650 can be located adjacent to the non-tissue facing surface and can include one or more second fixation elements 660. The second fixation elements 660 can be coiled or conformed into inner portions of an outer housing body 675 and can have tips 664 protruding into the guide apertures 627. In the illustrated retracted position 673 of the second fixation elements 660, the fixation mechanism assembly 615 can be positioned near a desired tissue site.

The fixation mechanism may or may not include one or more first fixation elements 630. If the first fixation elements 630 are present, the fixation mechanism assembly 615 can be pushed into tissue or pushed and rotated to embed the first fixation elements 630 into the tissue. The tissue facing surface 624 can be located adjacent to the tissue surface after the first fixation elements 630 have been embedded into the tissue.

The movable second fixation elements 660 can subsequently be deployed into the tissue by a relative movement between the first fixation member 620 and the second fixation member 650. In an example, the second fixation member 650 can be rotated in a clockwise direction 634 causing the second fixation element attachment 467 (FIG. 4A) to be brought closer to the guide apertures 627. As this movement takes place, tips 664 of the one or more second fixation elements 660 can move away from the guide apertures 627 and pierce or enter the tissue. Deployment of the moveable second fixation elements 660 can also be accomplished by a counter clockwise rotation 635 of the first fixation member 620 or a portion of the first fixation member, such as the ring member 621. The deployment of the second fixation elements 660 can also be accomplished by a combination of movements of the first fixation member 620 and the second fixation member 650.

The first fixation member 620 and the second fixation member 650 can include a radiopaque marker 678 that can be aligned when the one or more second fixation elements 660 are in a retracted position 673. Any non-alignment of the markers 678 can provide a measurable indication of the deployment of the second fixation elements 660. The relative positions of the radiopaque markers 678 can also provide a measureable indication of how far the second fixation elements 660 have entered the tissue. Deployment measurement can be important at tissue sites having thin membranes or regions for implantation of the fixation mechanism assembly 615.

One or more surfaces of the second fixation member 650 can include structural fixture features 676 that can aid in the movement of the second fixation member 650, or portions thereof during deployment or retraction of the one or more second fixation elements 660. These structural fixture features 676 can be located on external or internal surfaces of the second fixation member 650. The structural fixture features 676 can also or alternatively be located on external or internal surfaces of the first fixation member 620 to aid in movement of the first fixation member 620, or portions thereof.

Figure 7:
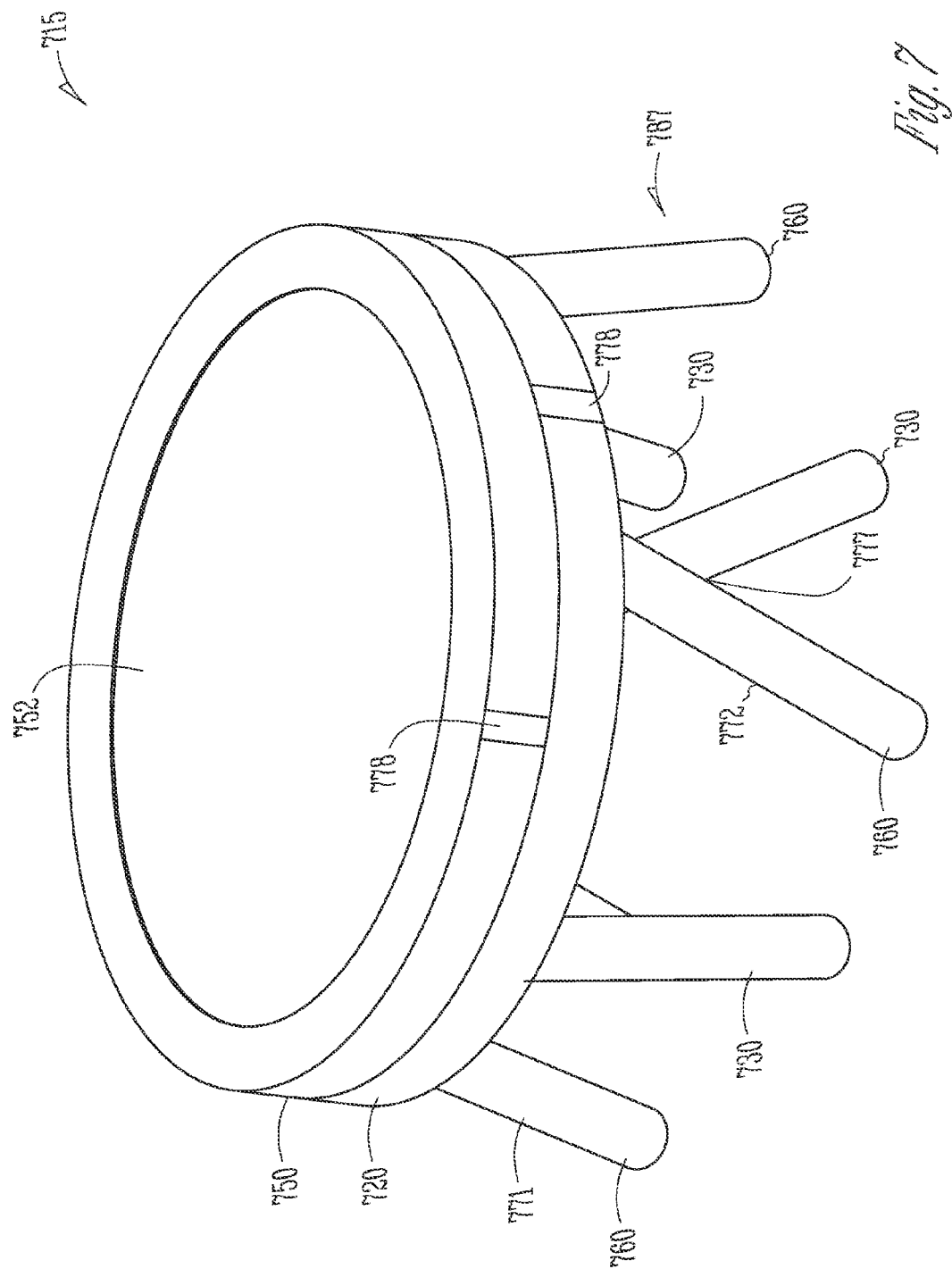
FIG. 7 illustrates an example of a fixation mechanism assembly with one or more second fixation elements in a deployed position, as constructed in accordance with at least one embodiment.

FIG. 7 is an illustration of a fixation mechanism assembly 715 including one or more second fixation elements 760 in a deployed position 772. A deployed shape of the second fixation elements 760 can vary from a retracted shape and can be tailored to a particular tissue site or use by altering shape memory characteristics of a material used for the second fixation elements 760. Radiopaque markings 778 on a first fixation member 720 and a second fixation member 750 can be not aligned providing a measureable indication to a surgeon or technician of the length of the second fixation elements 760 that have been deployed from the second fixation member 750.

In an example, a direction of one or more first fixation elements 730 points in a counter clockwise manner, while a direction of the one or more second fixation elements 760 points in a clockwise manner. In an example, such a directional configuration of the first and second fixation elements can provide a crossing 777 of the elements. The crossing can increase a gripping strength of the fixation mechanism assembly 715 to tissue. Positional differentiation between the first and second fixation elements can be accomplished in any manner that can aid in the gripping ability of the fixation mechanism assembly 715. In an example, the second fixation elements 760 can have a curved deployed shape rather than a straight deployed shape. The deployment of the second fixation elements 760 can cause interlocking between the first fixation elements 730 and the second fixation elements 760.

The second fixation member 750 can include a center section 752. The center section can include any auxiliary structure, feature or device, such as an electronic sensing device, a stimulation device, battery, circuitry, module, or power pack. These types of devices can also or alternatively be incorporated into the first fixation member 720. Any one or any combination of first fixation elements 720, the second fixation elements 760, portions of the first fixation member 720, or portions of the second fixation member 720 can be configured as an electrode or an array of electrodes. These structures can include one or more individually addressable electrodes. In an example, an electrode assembly 787 can include an electrode array that can include two or more electrodes. The electrode array can include electrodes that can be spatially distributed, such as according to a specified shape or orientation (e.g., in a linear array, a planar array, or a three-dimensional array). The electrodes can operate in pairs or groups. The electrodes can be connected to devices remote from the location of the fixation mechanism assembly 715.

One or more surfaces of the fixation mechanism assembly 715, or portions thereof, can be treated or configured to either promote tissue in-growth or slow down or exclude tissue in-growth. In an example, the fixation mechanism assembly 715 can be a permanent implantation and additional tissue in-growth can provide additional stability and securement. In an example, at least a portion of the fixation mechanism assembly 715 can be textured or porous, such as on a scale that can be configured to permit or facilitate tissue in-growth. For example, fibrotic tissue that can be formed around all or portions of the fixation mechanism assembly 715 can at least help more firmly hold the fixation mechanism assembly 715 against targeted tissue. In an example, fixation mechanism assembly 715 can include porous biomaterial or porous synthesized material, which can be attached to or covered on at least a portion of the first fixation elements 730, the second fixation elements 760, or outer surfaces of the first fixation member 720 or the second fixation member 750, such as to allow or promote tissue in-growth. Examples of the porous material can include one or more of: titanium or stainless steel fiber mesh, porous tantalum, or polyester or heavyweight polypropylene mesh, among others.

In an example, the fixation mechanism assembly 715 can be a temporary implantation or an implantation that may require servicing, maintenance, or repair and treatments or configurations that slow down or exclude tissue in-growth can allow all or portions of the fixation mechanism assembly to be easier to retract or remove. For example, a stimulation catheter or lead incorporating the fixation mechanism assembly 715 can be replaced or revised. As another example, untethered fixation mechanism 715, which can include sensing or stimulation devices, can have a depleted or near-depleted battery or other power source, thus prompting a device change out or device upgrade. To facilitate the detachment, at least some part of the fixation mechanism assembly 715 can be covered on its surface or otherwise provided with a surface that can include a material to inhibit tissue in-growth. An example of such material can include an expanded polytetrafluoroethylene (ePTFE) coating, such as with pores sized (e.g., <5 μm) to allow fluid to pass through, but not tissue and blood cells. Other examples of the tissue in-growth-inhibition material can include electrospun polyurethane or micro-textured material. The tissue in-growth-inhibition material can additionally or alternatively be coated on or otherwise provided at a portion of the fixation mechanism assembly 715, such as at the first fixation elements 730 or at surfaces of the first fixation member 720 or second fixation member 750, which contact tissue.

Figure 8:
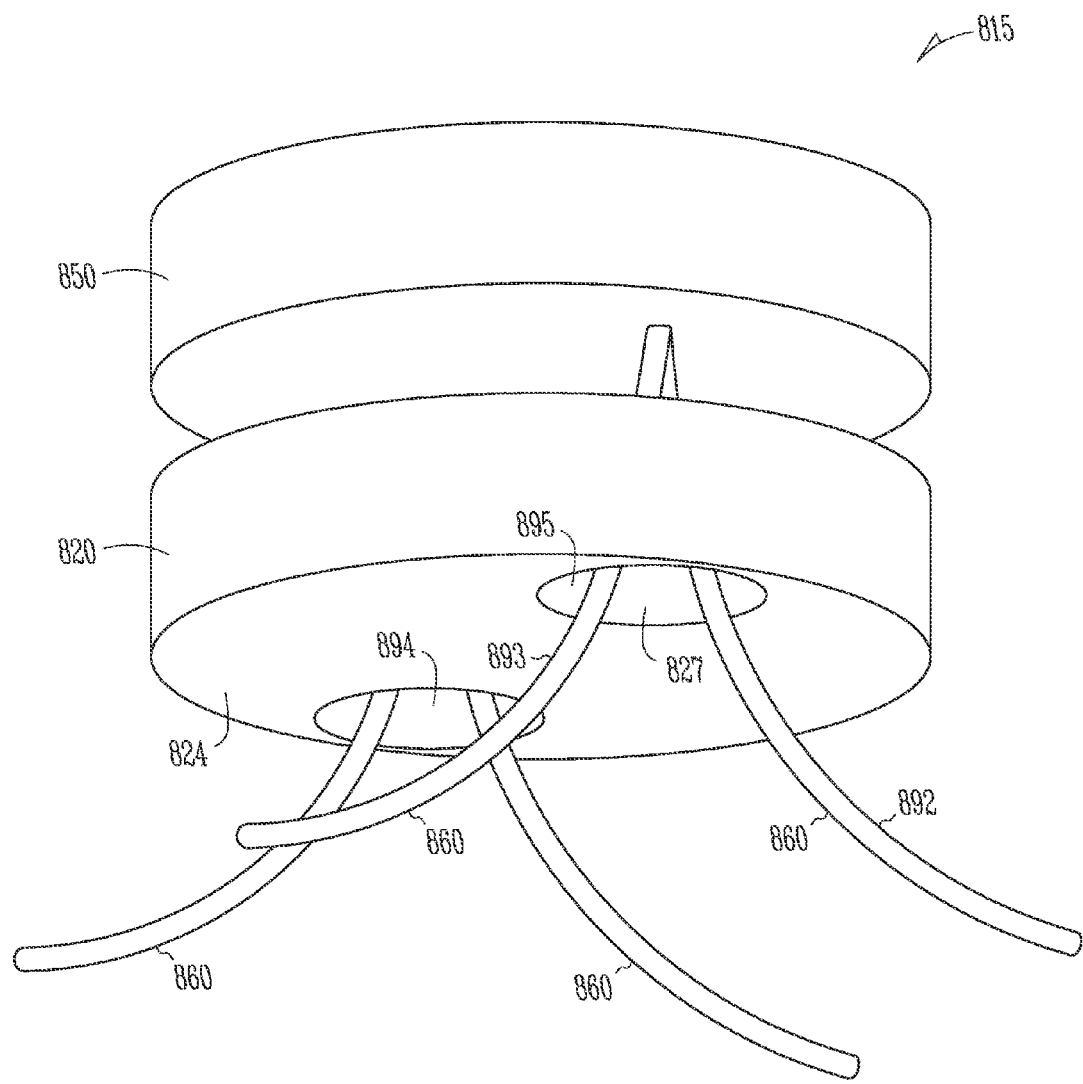
FIG. 8 illustrates an example of a fixation mechanism assembly, including a second fixation member having two or more second fixation elements configured to advance through a single guide aperture of a first fixation member, as constructed in accordance with at least one embodiment.

FIG. 8 illustrates an example of a fixation mechanism assembly 815 in which more than one second fixation element 860, included in a second fixation member 850, can be configured to pass through a single guide aperture 827 of a first fixation member 820.

The second fixation elements 860 can have different deployed geometry shapes, such as a first deployed shape 892 oriented towards a first direction (e.g., to the right), and a second deployed shape 893 oriented towards a second direction (e.g., to the left). These shapes can be controlled by shape memory alloys or by other manufacturing methods using materials flexible enough to conform to a desired retracted state and resilient enough to maintain a proper deployed geometry. The first deployed shape 892 and the second deployed shape 893 can have any geometry that can aid in securing the fixation mechanism assembly 815 to a tissue site. In an example, second fixation elements 860 deployed from a first guide aperture 894 can be configured to interlock or have intersecting axes with second fixation elements 860 deployed from a second guide aperture 895.

In some examples, the fixation mechanism assembly 815 can include a retracted state that does not include first fixation elements 730 (FIG. 7) protruding from a tissue facing surface 824 of the first fixation member 820. This type of configuration can be beneficial for intravenous introduction of the fixation mechanism assembly 815 into a body. The lack of first fixation elements can minimize catching or grabbing onto vessel walls or organ surfaces during introduction or movement of the fixation mechanism assembly 815 to a desired tissue site. The second fixation elements 860 can be fully retracted for movement through veins, arteries, or organs and have the same deployment gripping power as the above mentioned examples in which a first fixation element 730 crosses or intersects with a deployed second fixation element 760 (FIG. 7).

FIGS. 9-11 illustrate an example of fixation mechanism assemblies 1015, 1115. In these assemblies 1015, 1115, non-rotational movement between first and second fixation members causes deployment of one or more fixation elements.

In the example of FIG. 9, one or more second fixation elements 960 can be positioned in any location on a second fixation member 950 and can include a retaining structure 979 at their tips 964. The retaining structure 979 can, for example, include a barb 982. The tips 964 of first fixation elements or the second fixation elements 960 can additionally or alternatively include screw, hook, helix, or other tissue-penetrating mechanisms.

FIG. 10 illustrates an example of a fixation mechanism assembly 1015 in a retracted position 1073. In the retracted position 1073, tips 1064 of one or more second fixation elements 1060 are nested within one or more guide apertures 1027. A first fixation member 1020 can be moved relative to a second fixation member 1050 and the second fixation elements 1060 can be deployed from the guide apertures 1027 and can pierce tissue positioned under a tissue facing surface 1024 of the first fixation member 1020. In such an example, whereby a movement other than a rotation deploys fixation elements, the second fixation elements 1060 can include shape memory materials providing differentiation between geometries in a retracted and deployed configuration.

FIG. 11 illustrates a fixation mechanism assembly 1115 including one or more second fixation elements 1160 in a deployed position 1172. In the deployed position 1172, tips 1164 of the second fixation elements 1160 are extended from one or more guide apertures 1127 of a first fixation member 1120.

The above Detailed Description includes references to the accompanying drawings, which form a part of the Detailed Description. The drawings show, by way of illustration, specific embodiments in which the present fixation mechanism assemblies and corresponding methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or such that "A or B" includes "A but not B," "B but not A," and "A and B," unless otherwise indicated. In this document, the terms "proximal" and "distal" are used to refer to an assembly element location relative to a practitioner. For example, a proximal element portion is a portion closer to the practitioner of the assembly, whereas a distal element portion is a portion farther away from the practitioner of the assembly, such as the portions interacting with biological tissue.

In the appended claims, the terms "including" and "in which" are used as the plain-English equivalents of the respective terms "comprising" and "wherein." Also, in the following claims, the terms "including" and "comprising" are open-ended, that is, an assembly, kit, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A fixation mechanism assembly, comprising:
    a first fixation member including a housing having a tissue facing surface and an opposing non-tissue facing surface, one or more guide apertures extending between the tissue facing surface and the non-tissue facing surface, and one or more first fixation elements;
    the one or more first fixation elements including a longitudinal body and a proximal end attached to, or integrated with, the tissue facing surface of the housing of the first fixation member; and
    a second fixation member, moveably engaged with the first fixation member, including one or more second fixation elements,
    the one or more second fixation elements corresponding to the one or more guide apertures and each including a longitudinal body a proximal end attached to, or integrated with, the second fixation member, and a distal end movable through the one or more guide apertures.

2. The fixation mechanism assembly of claim 1, wherein the longitudinal body of one of the first fixation elements defines an axis that intersects with an axis defined by the longitudinal body of one of the second fixation elements.

3. The fixation mechanism assembly of claim 1, wherein the longitudinal body of the one or more first fixation elements includes a fixed length and a fixed angle, relative to the tissue facing surface of the housing of the first fixation member.

4. The fixation mechanism assembly of claim 1, wherein at least one of the one or more first fixation elements includes a rigid polymer and is electrically neutral.

5. The fixation mechanism assembly of claim 1, wherein the one or more guide apertures are located around a perimeter of the first fixation member.

6. The fixation mechanism assembly of claim 1, wherein the one or more second fixation elements are positioned to collectively surround the one or more first fixation elements.

7. The fixation mechanism assembly of claim 1, wherein a housing of the second fixation member is positioned adjacent the non-tissue facing surface of the housing of the first fixation member.

8. The fixation mechanism assembly of claim 1, wherein the one or more second fixation elements are extendable from, and retractable within, the tissue facing surface of the housing of the first fixation member through relative rotation between the first and second fixation members.

9. The fixation mechanism assembly of claim 1, wherein one or both of the first and second fixation members includes a stop feature configured to limit relative movement between the members.

10. The fixation mechanism assembly of claim 1, wherein at least one of the one or more second fixation elements is electrically neutral.

11. The fixation mechanism assembly of claim 1, wherein at least one of the one or more second fixation elements includes a shape memory alloy.

12. The fixation mechanism assembly of claim 1, wherein each of the one or more second fixation elements are configured to be deployed into a tissue site through rotation of the second fixation member relative to the first fixation member, and
    wherein, after deployment of the one or more second fixation elements, an axis defined by at least one of the one or more second fixation elements crosses an axis defined by at least one of the one or more first fixation element.

13. The fixation mechanism assembly of claim 1, wherein at least one of the one or more first or second fixation elements includes a radiopaque material.

14. The fixation mechanism assembly of claim 1, further comprising a fixation device configured to hold stationary one of the first fixation member and the second fixation member and rotate the other one of the first fixation member and the second fixation member.

15. A method of tissue fixation, comprising:
    engaging a first fixation member with a second fixation member, wherein the first fixation member includes one or more first fixation elements and the second fixation member includes one or more second fixation elements, and wherein the first fixation member further includes one or more apertures for receiving one or more of the second fixation elements of the second fixation member;
    positioning the first and second fixation members over a tissue site;
    engaging one or more of the first fixation elements of the first fixation member into the tissue site; and
    moving the first fixation member and the second fixation member in a predetermined manner relative to one another to deploy one or more of the second fixation elements of the second fixation member through one or more of the apertures of the first fixation member and into the tissue site.

16. The method of claim 15, wherein moving the first fixation member and the second fixation member in the predetermined manner relative to one another includes rotating one of the first fixation member and the second fixation member relative to the other one of the first fixation member and the second fixation member.

17. The method of claim 15, wherein deploying the one or more second fixation elements includes establishing a plurality of points of fixation between the first and second fixation members and the tissue site.

18. The method of claim 15, wherein one or more of the first fixation elements and/or one or more of the second fixation elements are operatively coupled to a sensing and/or stimulation device, and wherein the method further comprises using at least one of the first fixation elements and/or second fixation elements that are operatively coupled to the sensing and/or stimulation device to sense and/or stimulate the tissue site.

19. The method of claim 15, further comprising retracting the one or more second fixation elements from the tissue site through relative movement of the first fixation member and the second fixation member in a manner that is opposite the predetermined manner leading to deployment.

20. A fixation mechanism assembly, comprising:
a first fixation member including a housing having a tissue facing surface and an opposing non-tissue facing surface, one or more guide apertures extending between the tissue facing surface and the non-tissue facing surface, and one or more first fixation elements configured to attach the first fixation member to a body surface; and
a second fixation member, moveably engaged with the first fixation member, including one or more second fixation elements,
the one or more second fixation elements corresponding to the one or more guide apertures and each including an elongated body a proximal end attached to, or integrated with, the second fixation member, and a distal end movable through a corresponding one of the one or more guide apertures.

* * * * *